United States Patent [19]

Matsui et al.

[11] 4,327,223

[45] Apr. 27, 1982

[54] PROCESS FOR PRODUCING 1,3-DITHIOL-2-YLIDENE MALONATES

[75] Inventors: Hisanori Matsui, Nishinomiya; Hiroshi Tanaka; Kunihiro Yabutani, both of Neyagawa; Hitoshi Kurono, Toyonaka, all of Japan

[73] Assignee: Nihon Nohyaku Co., Ltd., Tokyo, Japan

[21] Appl. No.: 252,004

[22] Filed: Apr. 7, 1981

[51] Int. Cl.$^3$ .......................................... C07D 339/06
[52] U.S. Cl. ...................................................... 549/39
[58] Field of Search .......................................... 549/39

[56] References Cited

PUBLICATIONS

Takehana et al., Chem. Abstracts, vol. 91, (1979), 175322.

*Primary Examiner*—Henry R. Jiles
*Assistant Examiner*—Bernard Dentz
*Attorney, Agent, or Firm*—Cushman, Darby & Cushman

[57] ABSTRACT

A 1,3-dithiol-2-ylidene malonic acid dialkyl ester which was known as useful agricultural or horticultural fungicide and also as therapeutic agent for treating hepatic diseases can be prepared by a new process which comprises reacting a dialkyloxycarbonylketene dimercaptide with a trihalogenoethane in the presence of a base.

6 Claims, No Drawings

PROCESS FOR PRODUCING 1,3-DITHIOL-2-YLIDENE MALONATES

This invention relates to a process for producing 1,3-dithiol-2-ylidene malonic acid dialkyl esters. They are known compounds useful as agricultural or horticulatural fungicide and also as therapeutic agents for treating hepatic diseases.

Referring to the process for synthesizing the 1,3-dithiol-2-ylidene malonic acid dialkyl esters by use of malonic ester derivatives as one of the starting materials, for example, the following processes have been disclosed.

(1) Dehydration of corresponding 4-hydroxy-1,3-dithiolan-2-ylidene malonic acid dialkyl esters [Japanese patent application laid-open No. 48667 (1976)];

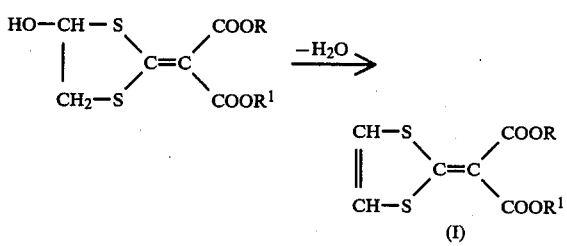

In this equation, R and $R^1$ are the same or different and each represents lower alkyl. The same definitions apply hereinafter.

(2) Reaction of corresponding dialkyloxycarbonylketene dimercaptides with a cis-1,2-halogenoethylene in an aprotic polar solvent [Japanese patent application laid-open No. 63085 (1979)]:

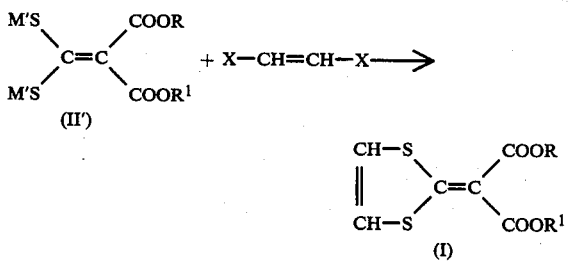

In this equation, M' and X represent alkali metal and halogen, respectively.

In process (1), the starting compounds 4-hydroxy-1,3-dithiolan derivatives are required to synthesize from substituted ketene mercaptides represented by formula (II'), which are the starting materials of process (2). Therefore, process (1) has the disadvantage that the overall manufacturing process is longer as compared with process (2). Meanwhile, any 1,2-cis-dihalogenoethylene used in process (2) is at present not commercially available as an industrial raw material. Hence, it must be specially manufactured and then would be expensive. Moreover, it is difficult to obtain in a purified form and involves the problem of isomerization. Thus both prior arts admit of improvements in technical and economical aspects.

Recently, the present inventors have found that dialkyloxycarbonylketene dimercaptides, which can be obtained by the reaction of dialkyl malonates with carbon disulfide, react with a trihalogenoethane to accomplish ring closure thus giving 1,3-ditiol-2-ylidene malonic acid dialkyl esters. This reaction can be schematically represented as follows:

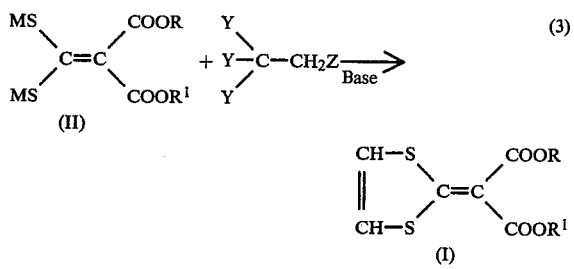

In this equation, M is alkali metal or ammonium, Y is halogen, and Z is halogen or hydrogen, with the proviso that either one of two 2 is invariably hydrogen. R and R' are as defined above.

Dialkyloxycarbonylketene dimercaptides represented by formula (II) can be synthesized by the known reaction (4):

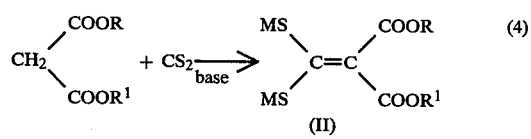

In this equation, R, $R^1$, and M are as defined above.

The base ions represented by M in a ketene mercaptide, used in this invention, of formula (II) come from the base material used in the reaction of a dialkyl malonate with carbon disulfide, as can be seen from equation (4) schematically shown above. While any base material having reactivity toward a trihalogenoethane can be used in this invention, typical examples of the mercaptan salts in the formula (II) are dipotassium salt and disodium salt. Besides these salts, diammonium salt can be used in the process of this invention.

The ester moieties of a compound represented by formula (II) come from the dialkyl malonate used in reaction (4) given above. In this case, the two lower alkyls may be the same or different. Both the lower alkyls include $C_1$–$C_5$ alkyls such as, for example, methyl, ethyl, n-propyl, isopropyl, n-butyl, isobutyl, s-butyl, t-butyl, and isoamyl. Consequently, the compounds represented by formula (II) include the ketene mercaptides derived from the following malonates: dimethyl malonate, diisopropyl malonate, diethyl malonate, di-n-propyl malonate, diallyl malonate, di-n-butyl malonate, diisobutyl malonate, di-t-butyl malonate, di-s-butyl malonate, methyl isopryl malonate, methyl n-propyl malonate, ethyl n-butyl malonate, methyl ethyl malonate, ethyl isopropyl malonate, methyl isobutyl malonate, etc. A typical one of these malonates is diisopropyl malonate, and consequently typical dialkyloxycarbonylketene mercaptides of formula (II) include:

Diisopropoxycarbonylketene disodium mercaptide

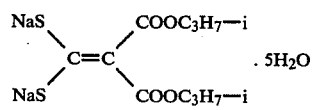

[pale yellow crystal; m.p. 183° C. or more (yellowing)]

Diisopropoxycarbonyl ketene dipotassiummercaptide

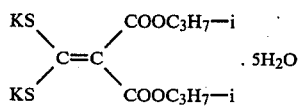

(pale yellow crystal; discolors at 102°–109° C. while foaming; decomposes into black matter at 300° C. or more.)

Trihalogenoethanes to be used in this invention include 1,1,1-trichloroethane, 1,1,1-tribromoethane, 1,1-dichloro-2-chloroethane, 11-dichloro-2-bromoethane, and 1,1,2-tribromo-bromoethane. Of these trihalogenoethanes, 1,1,1-trichloroethane is most advantageous since it gives better yields and also is inexpensive.

Process (3) of this invention can be accomplished by reacting a ketene mercaptide of formula (II) with a trihalogenoethane in the presence of a base. This reaction is an equimolar one, but one of the reactants, either ketene mercaptide or trihalogenoethane, may also be used in excess; for example, a trihalogenoethane is used in an amount ratio of 1 to 8 moles per mole of the ketene mercaptide used, in particular, the molar ratio range of 2 to 4 is preferable by reason that, for example, it gives higher yields.

The above reaction (3) of this invention is carried out in the presence of a suitable base material, for example, alkali metal hydroxide such as potassium hydroxide, sodium hydroxide and alkali earth metal hydroxide such as calcium hydroxide, magnesium hydroxide. The preferred amount of the base is 1 to 2 moles per mole of the reaction taking place. Such a base material can be used in the form of solution or solid such as powder, but the form of solution is preferable, for example, with respect to handling.

Any solvent, unless inhibitory against this reaction, can be used; in particular, a mixture of water with a polar solvent is desirable. As examples of the polar solvent, may be cited dimethylsulfoxide, N-methylpyrrolidone, dimethylformamide, N,N-dimethylacetamide, hexamethylphosphoramide, and Sulforane (tetrahydrothiophen-1,1-dioxide). In addition, chloroform can be used. Of these solvents, dimethylsulfoxide is the most preferred one. Accordingly, the most preferred solvent system to be used in this reaction is a mixture of water with dimethylsulfoxide. The water in this mixture generally comes from the aqueous solution of a base mentioned above.

In carrying out the process of this invention, reaction temperature can be selected suitably from within the range of about 10° C. to the boiling region of the solvent system. Usually, the reaction is better carried out between room temperature and about 80° C., and preferably at 50° C. to 80° C.

After completion of the reaction, the object matter can be isolated according to a usual separation method; for instance, by extraction from the resulting reaction mixture into a suitable solvent, followed by applying a suitable method to remove the solvent, the object matter can be obtained.

Meanwhile, it has been found that the above ketene mercaptide which has been obtained as a reaction mixture on synthesis can be used as it is, in other words, without isolating said mercaptide, for the ring closure reaction. This method will be illustrated hereinbelow.

When a dialkyl malonate is reacted with carbon dulsulfide in the presence of a base, the corresponding dialkyloxycarbonylketene dimercaptide can be obtained in the reaction fluid nearly quantitatively. Said ketene dimercaptide can also be obtained in an alkali-water solvent [Japanese patent application laid-open Nos. 99110 (1973) and 24265 (1975)] or in a polar solvent [Japanese patent application laid-open No. 13174 (1974)].

Thus, this invention also provides a process for producing 1,3-dithiol-2-ylidene malonic acid dialkyl esters by reacting dialkyl malonates with carbon disulfide in the presence of a base and successively with a trihalogenoethane. The reaction of dialkyl malonates with carbon disulfide proceeds satisfactorily in a polar solvent, but in the successive reaction with a trihalogenoethane the addition of water is desirable. Accordingly, this process is conveniently carried out in a mixture of water with a polar solvent from the beginning. The water in this case is generally brought from the aqueous solution of the base. The process of this invention involves the following embodiments, but is not limited thereto:

(1) Required amounts of a dialkyl malonate, carbon disulfide, and of a trihalogenoethane are put together with a polar solvent in a vessel, and a required amount of an aqueous solution of a base is added thereto, whereby reaction is carried out.

(2) Required amounts of a dialkyl malonate and of carbon disulfide are put in a polar solvent, an aqueous solution of a base and subsequently a trihalogenoethane alone or dissolved in a polar solvent are added thereto, and if necessary, an aqueous solution of a base is further added, whereby reaction is carried out.

(3) To a mixture of required amounts of a dialkyl malonate and of carbon disulfide, an aqueous solution of a base and subsequently a polar solvent containing a required amount of a trihalogenoethane are added thereto, and if necessary, an aqueous solution of a base is further added, whereby reaction is carried out.

(4) A resulting mixture of the reaction of a dialkyl malonate with carbon disulfide and an aqueous solution of a base is added to a polar solvent containing a required amount of a trihalogenoethane, whereby reaction is carried out.

In carrying out the process of this invention, carbon disulfide may be used in an amount of 0.9 to 1.2 moles per mole of the dialkyl malonate, and the base throughout the whole reaction may be used in an amount of 3 to 5 moles per mole of the dialkyl malonate used. The base may also be added in parts, for instance, at a molar ratio of nearly from 2 to 3 in the reaction of the dialkyl malonate with carbon disulfide and at a molar ratio of nearly from 1 to 2 in the reaction with the trihalogenoethane, based on the amount of the dialkyl malonate used. When the base is added in limited amounts according as the reaction proceeds, an improved yield is often obtained. Preferred examples of the base are sodium hydroxide and potassium hydroxide, and the latter is particularly preferable.

The reaction of a dialkyl malonate with carbon disulfide is desirable to start at a temperature not exceeding 30° C. since it is exothermic, and thereafter it may be carried out at a temperature of about 50° to 80° C.

After completion of the reaction, the object matter may be isolated by the method mentioned above.

The following compounds are typical examples that can be synthesized according to the process of this invention. These compounds are shown in terms of R and $R^1$ in the formula:

$$\begin{array}{c} CH-S \\ \| \\ CH-S \end{array} C=C \begin{array}{c} COOR \\ \\ COOR^1 \end{array}$$

| No. | R | $R^1$ | Melting point or refractive index |
| --- | --- | --- | --- |
| 1 | $CH_3$ | $CH_3$ | m.p. 134.5–135°C. |
| 2 | $C_2H_5$ | $C_2H_5$ | m.p. 113° C. |
| 3 | i-$C_3H_7$ | i-$C_3H_7$ | m.p. 60.5° C. |
| 4 | n-$C_3H_7$ | n-$C_3H_7$ | m.p. 73–75° C. |
| 5 | i-$C_4H_9$ | i-$C_4H_9$ | m.p. 76–78° C. |
| 6 | n-$C_4H_9$ | i-$C_4H_9$ | m.p. 55–57° C. |
| 7 | $C_2H_5$ | i-$C_3H_7$ | m.p. 57–58° C. |
| 8 | $CH_3$ | i-$C_4H_9$ | $n_D^{20}$ 1,5928 |

EXAMPLE 1

Diisopropoxycarbonylketene disodium mercaptide crystals (8 g, 0.02 mol) was dissolved in 50 ml of dimethylsulfoxide, and 1,1,1-trichloroethane (2.7 g, 0.02 mol) and subsequently a 30% sodium hydroxide aqueous solution (2.7 g, 0.02 mol NaOH) were added thereto. Thus, reaction was carried out at 60° C. for 1 hour. The resulting mixture was poured into ice-water, and then extracted with benzene. Drying of the extract over anhydrous magnesium sulfate, distillation to remove benzene, and recrystallization from n-hexane gave 2.6 g of the object matter diisopropyl 1,3-dithiol-2-ylidene malonate; m.p. 60.5° C., yield 45%.

EXAMPLE 2

Diisopropyl malonate (18.8 g, 0.1 mol) and carbon disulfide (7.6 g, 0.1 mol) were dissolved in 200 ml of dimethylsulfoxide. Dropping thereto a 45% potassium hydroxide aqueous solution (31 g, 0.25 mol KOH) at 13°–17° C., gave a yellowish red solution containing diisopropoxycarbonylketene dipotassium mercaptide. At 20° C., 1,1,1-trichloroethane (26.6 g, 0.2 mol) was added, and 5 minutes after a 45% potassium hydroxide aqueous solution (18.6 g, 0.15 mol KOH) was dropped thereinto. The temperature was raised to 70° C. to carry out reaction for 30 minutes. The resulting mixture was poured into ice-water and then extracted with benzene. Drying of the extract over anhydrous magnesium sulfate, distillation to remove benzene, and recrystallization from n-hexane gave 23.6 g of the object matter diisopropyl 1,3-dithiol-2-ylidene malonate; m.p. 60.5° C., yield 82.1%.

EXAMPLE 3

Diisopropyl malonate (18.8 g, 0.1 mol) and carbon disulfide (7.6 g, 0.1 mol) were dissolved in 200 ml of dimethylsulfoxide. A 45% potassium hydroxide aqueous solution (49.6 g, 0.4 mol KOH) was dropped thereto at 15° C., then 1,1,1-trichloroethane (13.3 g, 0.1 mol) was added at 20° C., and reaction was carried out at 70° C. for 30 minutes. The resulting mixture was poured into ice-water and then extracted with benzene. Drying of the extract over anhydrous magnesium sulfate, distillation to remove benzene, and recrystallization from n-hexane gave 18.1 g of the object matter diisopropyl 1,3-diethiol-2-ylidene malonate; m.p. 60.5° C., yield 62.8%.

In the same manner except for using 1,1,2-trichlorethane (13.3 g, 0.1 mol), 15 g of the object matter was obtained; yield 52%.

Further, in the same manner except for using 1,1-dichloro-2-bromoethane (35.6 g, 0.2 mol), 11.5 g of the object matter was obtained; yield 39.9%.

Still further, in the same manner except for using 1,1,2-tribromoethane (52.4 g, 0.2 mol), 12.9 g of the object matter was obtained; yield 44.8%.

EXAMPLE 4

Diethyl malonate (16 g, 0.1 mol) and carbon disulfide (7.6 g, 0.1 mol) were dissolved in 200 ml dimethylsulfoxide. Dropping of a 45% potassium hydroxide aqueous solution (31 g, 0.25 mol KOH) thereto at 15°–20° C. gave a solution containing diethooxycarbonylketene dipotassium mercaptide, to which 1,1,1-trichloroethane (39.9 g, 0.3 mol) was added at 20° C. and a 45% potassium hydroxide aqueous solution (18.6 g, 0.15 mol KOH) was dropped at 40° C. The temperature was raised to 70° C. to continue reaction for 20 minutes. The resulting mixture was poured into ice-water, followed by extraction with benzene. Drying of the extract over anhydrous magnesium sulfate, distillation to remove benzene, and recrystallization from n-hexane gave 17.8 g of the object matter diethyl 1,3-dithio-2-ylidene malonate; m.p. 113° C., yield 68.5%.

EXAMPLE 5

Dropping a 45% potassium hydroxide aqueous solution (36.6 g, 0.3 mol KOH) into a mixture of di-n-butyl malonate (21.6 g, 0.1 mol) with carbon disulfide (7.6 g, 0.1 mol) at 20° C. gave a solution containing di-n-butoxycarbonylketene dipotassium mercaptide. Thereto, a 200 ml dimethylacetamide solution containing 1,1,1-trichloroethane (26.6 g, 0.2 mol) was added, and further a 45% potassium hydroxide aqueous solution (12.4 g, 0.1 mol KOH) was added at 30° C. to carry out reaction at 60° C. for 1 hour. The resulting mixture was poured into ice-water, followed by extraction with benzene. Drying of the extract over anhydrous magnesium sulfate, distillation to remove benzene, and recrystallization from n-hexane gave 12.6 g of the object matter di-n-butyl 1,3-dithiol-2-ylidene malonate; m.p. 55°–57° C., yield 40%.

EXAMPLE 6

Dropping a 45% potassium hydroxide aqueous solution (31 g, 0.25 mol KOH) into a mixture of dimethyl malonate (13.2 g, 0.1 mol) with carbon disulfide (7.6 g, 0.1 mol) while keeping the temperature not exceeding 20° C. gave a solution containing dimethoxy carbonylketene dipotassium mercaptide. After pouring of 300 ml of acetone thereto, the resulting liquid was left at −5° C. for 2 hours to separate the dipotassium salt crystals out. The crystals were collected by filtration, washed with a small amount of acetone, and added to a dimethylsulfoxide solution containing 1,1,1-trichloroethane (26.6 g, 0.2 mol). After addition of a 45% potassium hydroxide aqueous solution (12.4 g, 0.1 mol KOH) thereto at 30° C., reaction was carried out at 60° C. for 1 hour. The resulting mixture was poured into ice-water and then extracted with benzene. Drying of the extract over anhydrous magnesium sulfate, distillation to remove benzene, and recrystallization from n-hexane gave 8.5 g of dimethyl 1,3-dithiol-2-ylidene malonate; m.p. 134.5°–135.0° C., yield 36.5%.

EXAMPLE 7

Diisopropyl malonate (18.8 g, 0.1 mol), carbon disulfide (7.6 g, 0.1 mol), and 1,1,1-trichloroethane (26.6 g, 0.2 mol) were added to 200 ml of dimethylsulfoxide, and a 35% potassium hydroxide aqueous solution (64 g, 0.4 mol KOH) was dropped thereto at 30° C. or less. Then, the mixture was heated to 60° C. to continue reaction for 30 minutes. The resulting mixture was poured into ice-water, and then extracted with benzene. Drying of the extract over anhydrous magnesium sulfate, distillation to remove benzene, and recrystallization from n-hexane gave 20.7 g of the object matter; m.p. 60.5° C., yield 72%.

EXAMPLE 8

Diisopropyl malonate (188 g, 1.0 mol) and carbon disulfide (76 g, 1.0 mol) were dissolved in 3 l of dimethylsulfoxide. A yellowish red suspension containing diisopropoxycarbonylketene dipotassium mercaptide was obtained by dropping a 48.5% potassium hydroxide aqueous solution (243 g, 2.1 mol KOH) thereto at about 20° C. To this suspension 1,1,1-trichloroethane (213.4 g, 1.6 mol) was added, and successively a 48.5% potassium hydroxide aqueous solution (127.2 g, 1.1 mol KOH) and 89.4 g of water were dropped at 25°-30° C. spending 30 minutes. Thereafter, the reaction mixture was allowed to stand at 30°-35° C. for 30 minutes under stirring and then was heated at 75° C. for 20 minutes to complete reaction. The resulting mixture was cooled to room temperature, and thereafter filtered to remove the formed crystalline solid. The filtrate was admixed with 600 ml of water and then extracted with cyclohexane. Washing of the cyclohexane layer with water, followed by distillation to remove cyclohexane, gave 237 g of diisopropyl 1,3-dithiol-2-ylidene malonate; m.p. 60.5° C., yield 82.2%.

EXAMPLE 9

A pale yellow-solution containing diisopropoxycarbonylketene dipotassium mercaptide was obtained by dropping a 48.5% potassium hydroxide aqueous solution (243 g, 2.0 mol KOH) to a mixture of diisopropyl malonate (188 g, 1.0 mol) with carbon disulfide (76 g, 1.0 mol) while keeping the temperature not exceeding 20° C. This solution, after admixed further with a 36% potassium hydroxide aqueous solution (211 g, 1.4 mol KOH), was dropped to a solution prepared by dissolving 1,1,1-trichlorethane (186.8 g, 1.4 mol) in 3.2 l of dimethylsulfoxide, spending 45 minutes while keeping the temperature at 20° C.

After completion of the dropping, the solution was heated and kept at 70° C. for 15 minutes to complete reaction. The resulting mixture was cooled to room temperature and filtered to remove the formed crystalline solid. The filtrate was extracted with 3 l of 1,1,1-trichloroethane. Washing of the trichloroethane layer with water, followed by distillation to remove trichloroethane, gave 243 g of the object matter; m.p. 60.5° C., yield 84.3%.

EXAMPLE 10

A 48.5% potassium hydroxide aqueous solution (253.6 g, 2.2 mol KOH) was slowly dropped to a mixture of 1,1,2-trichloroethane (280 g, 2.1 mol) with isopropanol (118 g, 2.0 mol) at a temperature not exceeding 30° C. spending 6 hours. To this solution, was added 2.6 l of dimethylsulfoxide and further was dropped a diisopropoxycarbonylketene dipotassium mercaptide solution at 14°-15° C. spending 70 minutes, said mercaptide solution being prepared separately by dropping a 48.5% potassium hydroxide aqueous solution (253.6 g, 2.2 mol KOH) to a mixture of diisopropyl malonate (188 g, 1.0 mol) with carbon disulfide (76 g, 1.0 mol) at a temperature not exceeding 20° C. This reaction mixture was allowed to stand for 1 hour at a temperature not exceeding 20° C. and for further 2 hours at room temperature and then heated to react at 70° C. for 20 minutes. The resulting mixture was cooled to room temperature and filtered to remove the formed crystalline solid. The filtrate was admixed with 800 ml of water and extracted twice with 3 l each of cyclohexane. Washing of the extract with water, followed by distillation to remove the solvent, gave 244.9 g of the object matter; m.p. 60.5° C., yield 84.9%.

EXAMPLE 11

Diisopropyl malonate (188 g, 1.0 mol), carbon disulfide (76 g, 1.0 mol), and 1,1,1-trichloroethane (267 g, 2.0 mol) were dissolved in 1.1 l of dimethylsulfoxide. A 48.5% potassium hydroxide aqueous solution (417 g, 3.6 mol KOH) was dropped thereto at 20°-25° C. spending 30 minutes. Thereafter, the reaction temperature was kept at 30°-35° C. for 30 minutes and then at 75° C. for 15 minutes to complete reaction.

The resulting mixture was cooled to room temperature, and thereafter filtered to remove the precipitated salt. The filtrate was admixed with 350 ml of water and extracted twice with 1 l each of cyclohexane. The cyclohexane layer was washed with water, dehydrated, concentrated to ⅔ of original volume thereof, stirred with 40 g of an active carbon powder at 50° C. for 30 minutes, and hot-filtered. Distillation of the filtrate to remove cyclohexane, followed by recycrestallization from n-hexane, gave faintly yellow crystals of diisopropyl 1,3-dithiol-2-ylidene malonate; m.p. 60.5° C., yield 70%.

EXAMPLE 12

Diisopropyl malonate (18.8 g, 0.1 mol) and carbon disulfide (7.6 g, 0.1 mol) were dissolved in 200 ml of dimethylsulfoxide, and a 48.5% potassium hydroxide aqueous solution (24.3 g, 0.21 mol KOH) was dropped thereto at about 20° C. to prepare a yellowish red suspension containing diisopropoxycarbonylketene dipotassium mercaptide. This suspension, after addition of 1,1,1-trichloroethane (13.3 g, 0.1 mol) at 25° C., was heated to 35° C., stirred for 30 minutes, and further heated to react at 70° C. for 20 minutes.

The resulting mixture was cooled to room temperature, admixed with ice-water to dissolve the precipitated salt, and extracted with 400 ml of ether. Washing of the extract with water, followed by distillation to remove the solvent, gave 8.7 g of the object matter; m.p. 60.5° C., yield 30.3%.

EXAMPLE 13

Diisopropyl malonate (18.8 g, 0.1 mol), carbon disulfide (7.6 g, 0.1 mol), and 1,1,1-trichloroethane (26.7 g, 0.2 mol) were dissolved in 200 ml chloroform. A 48.5% potassium hydroxide aqueous solution (46.3 g, 0.4 mol KOH) was dropped thereto at a temperature not exceeding 20° C. The reaction mixture was then heated slowly to reflux for 30 minutes. The resulting mixture was cooled to room temperature, washed with water, and distilled to remove the solvent. Acetone was added to the solid residue obtained, and acetone-insoluble components were filtered off. Concentration of the filtrate, followed by recrystallization of the concentrated residue from n-hexane, gave 5.8 g of the object matter; m.p. 60.5° C., yield 20%.

In the same manner as the above except for using dimethylacetamide as solvent in place of chloroform, 7.1 g of the object matter was obtained; yield 24.7%.

EXAMPLE 14

Diisopropyl malonate (18.8 g, 0.1 mol) and carbon disulfide (7.6 g, 0.1 mol) were dissolved in 110 ml of dimethylsulfoxide. Addition of powdered potassium hydroxide (13.9 g, 0.21 mol) thereto, followed by reaction at 60°-70° C. for 30 minutes, gave a yellowish red solution containing diisopropoxycarbonylketene dipotassium mercaptide. To this solution, 1,1,1-trichloroethane (26.7 g, 0.2 mol) was added at 25° C., and then a 48.5% potassium hydroxide aqueous solution (17.4 g, 0.15 mol KOH) was dropped at 25°-30° C. The reaction mixture was stirred at 30°-35° C. for 30 minutes and then heated to continue reaction at 70° C. for 30 minutes.

The resulting mixture was filtered to remove the precipitated salt, admixed with 30 ml of water, and extracted with 200 ml of cyclohexane. Washing of the extract with water, followed by distillation to remove the solvent, gave 20.3 g of the object matter; m.p. 60.5° C., yield 70.5%.

EXAMPLE 15

Diisopropyl malonate (18.9 g, 0.1 mol) and carbon disulfide (7.6 g, 0.1 mol) were dissolved in 120ml of dimethylsulfoxide. Dropping of a 48.5% potassium hydroxide aqueous solution (24.3 g, 0.21 mol KOH) thereto at about 20° C. gave a yellowish red suspension containing diisopropoxycarbonylketene dipotassium mercaptide. This suspension, after addition of 1,1,1-trichloroethane (26.7 g, 0.2 mol), was warmed to 30° C., and powdered potassium hydroxide (10 g, 0.15 mol) was added thereto. This reaction mixture was stirred at 30°-40° C. for 30 minutes, and further heated to continue reaction at 75° C. for 20 minutes. The resulting mixture, after cooled to room temperature, was admixed with ice-water to dissolve the precipitated salt, and extracted with 200 ml of diethyl ether. Washing of the extract with water, followed by distillation to remove diethyl ether, gave 20.8 g of the object matter; m.p. 60.5° C., yield 72.3%.

What is claimed is:

1. A process for producing 1,3-dithiol-2-ylidene malonic acid dialkyl esters which is characterized by reacting a dialkyloxycarbonylketene dimercaptide with a trihalogenoethane in the presence of a base.

2. A process of claim 1, wherein said reaction is carried out in a polar solvent.

3. A process of claim 2, wherein said polar solvent is dimethylsulfoxide.

4. A process for producing 1,3-dithiol-2-ylidene malonic acid dialkyl esters, which is characterized by reacting a dialkyl malonate, in the presence of a base, with carbon disulfide and successively with a trihalogenoethane.

5. A process of claim 4, wherein said reaction is carried out in a polar solvent.

6. A process of claim 5, wherein said polar solvent is dimethylsulfoxide.

* * * * *